US006260188B1

(12) United States Patent
Ungpiyakul et al.

(10) Patent No.: US 6,260,188 B1
(45) Date of Patent: Jul. 10, 2001

(54) CONTROL MODEL

(75) Inventors: Tanakon Ungpiyakul, Neenah; Anne Marie Lindeke, Hortonville; Thomas Arthur Bett, Oshkosh, all of WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 0 days.

(21) Appl. No.: 09/224,273

(22) Filed: Dec. 31, 1998

(51) Int. Cl.$^7$ ................................................. G06F 9/445
(52) U.S. Cl. ................................................. 717/1; 717/1
(58) Field of Search .............................. 327/170; 318/38; 706/13; 717/1, 4, 11

(56) References Cited

U.S. PATENT DOCUMENTS

| 4,514,846 | 4/1985 | Federico et al. | 371/16 |
|---|---|---|---|
| 4,837,715 | 6/1989 | Ungpiyakul et al. | 364/552 |
| 5,045,135 | 9/1991 | Meissner et al. | 156/64 |
| 5,138,377 | 8/1992 | Smith et al. | 355/207 |
| 5,195,029 | 3/1993 | Murai et al. | 364/184 |
| 5,200,779 | 4/1993 | Nawata | 355/206 |
| 5,218,406 | 6/1993 | Ebner | 355/205 |
| 5,239,547 | 8/1993 | Tomiyama et al. | 371/16.4 |
| 5,251,273 | 10/1993 | Betts et al. | 382/57 |
| 5,286,543 | 2/1994 | Ungpiyakul et al. | 428/74 |
| 5,315,697 | 5/1994 | Nagamatsu | 395/155 |
| 5,333,062 | 7/1994 | Hara et al. | 358/437 |
| 5,359,525 | 10/1994 | Weyenberg | 364/469 |
| 5,365,310 | 11/1994 | Jenkins et al. | 355/202 |
| 5,388,252 | 2/1995 | Dreste et al. | 395/575 |

(List continued on next page.)

FOREIGN PATENT DOCUMENTS

| 0 485 691 B1 | 5/1992 | (EP) | B26D/5/34 |
|---|---|---|---|
| 2044792 | 5/1992 | (CA) | G05D/5/04 |
| 0 657 852 A2 | 6/1995 | (EP) | G06T/1/20 |
| 9081233 | 3/1997 | (JP) | G05B/23/02 |
| WO 93/07445 | 4/1993 | (WO) | G01B/21/14 |

OTHER PUBLICATIONS

Acquiring and Displaying Images, COGNEX, pp. 34–35, 136–138, 143, 146–148, 153–154, and 530. Date unknown.

"User's Manual Model 1012," Kodak Ektapro EM Motion Analyzer, Eastman Kodak Company, 1990. pp. 1.1–7.9.

*Primary Examiner*—Mark Powell
*Assistant Examiner*—Michael B. Holmes
(74) *Attorney, Agent, or Firm*—Thomas D. Wilhelm; Paul Y. Yee

(57) ABSTRACT

Methods of controlling processes having operating conditions, one or more inputs, and one or more outputs. The methods comprise defining acceptable steady state conditions, operating the process, and sampling output on the basis of a dual segment output population model, detecting destabilizing process events which result in output not representing acceptable output parameters, defining operating conditions according to which output is rejected, and defining output parameters according to which output is rejected. Upon detecting a destabilizing process event, the invention temporarily implements sampling assuming a second segment of the output population. The process can include automatically rejecting output whenever any one of either the operating conditions or the output parameters is violated, thereby establishing a leading automatic output rejection and a trailing automatic output rejection in relation to the destabilizing event, and thus defining an automatic output rejection period according to which output is automatically rejected. Such embodiments define a leading transition period proximate and prior to the automatic output rejection period, and a trailing transition period proximate and after the automatic output rejection period. The transition periods, overall, represent periods of higher than average risk that output will be defective. The method contemplates automatically sampling output in at least one of the leading transition period and the trailing transition period.

49 Claims, 4 Drawing Sheets

U.S. PATENT DOCUMENTS

| | | | |
|---|---|---|---|
| 5,388,618 | 2/1995 | Decock | 139/1 R |
| 5,392,095 | 2/1995 | Siegel | 355/200 |
| 5,437,278 | 8/1995 | Wilk | 128/653.1 |
| 5,452,438 | 9/1995 | Umeda et al. | 395/180 |
| 5,467,355 | 11/1995 | Umeda et al. | 364/571.04 |
| 5,469,553 * | 11/1995 | Patrick | 395/750 |
| 5,490,089 | 2/1996 | Smith et al. | 364/514 R |
| 5,564,005 | 10/1996 | Weber et al. | 395/161 |
| 5,619,445 | 4/1997 | Hyatt | 365/45 |
| 5,659,538 | 8/1997 | Stuebe et al. | 364/469.02 |
| 5,694,528 | 12/1997 | Hube | 395/113 |
| 5,841,530 | 11/1998 | Hewitt et al. | 356/237 |

* cited by examiner

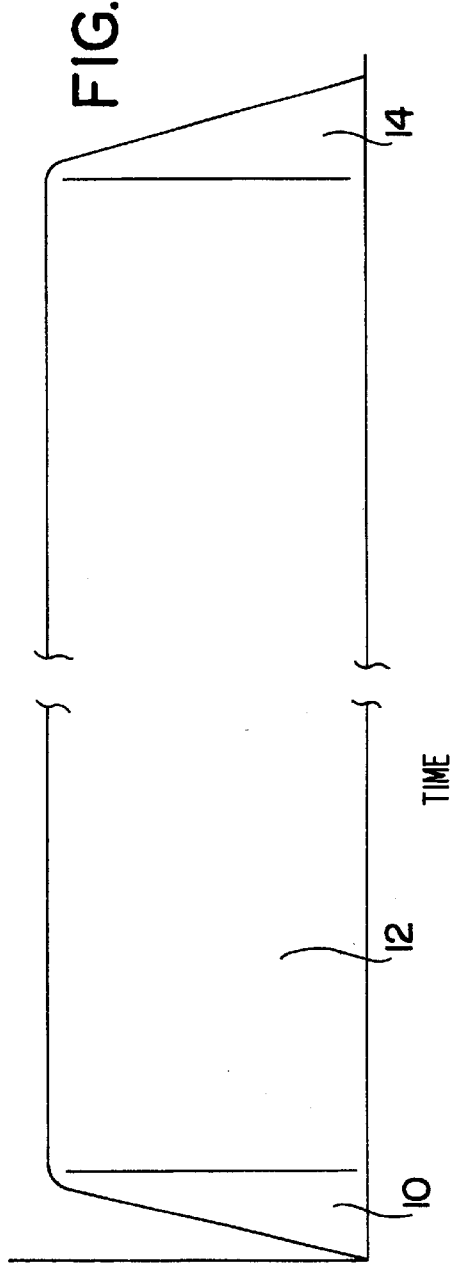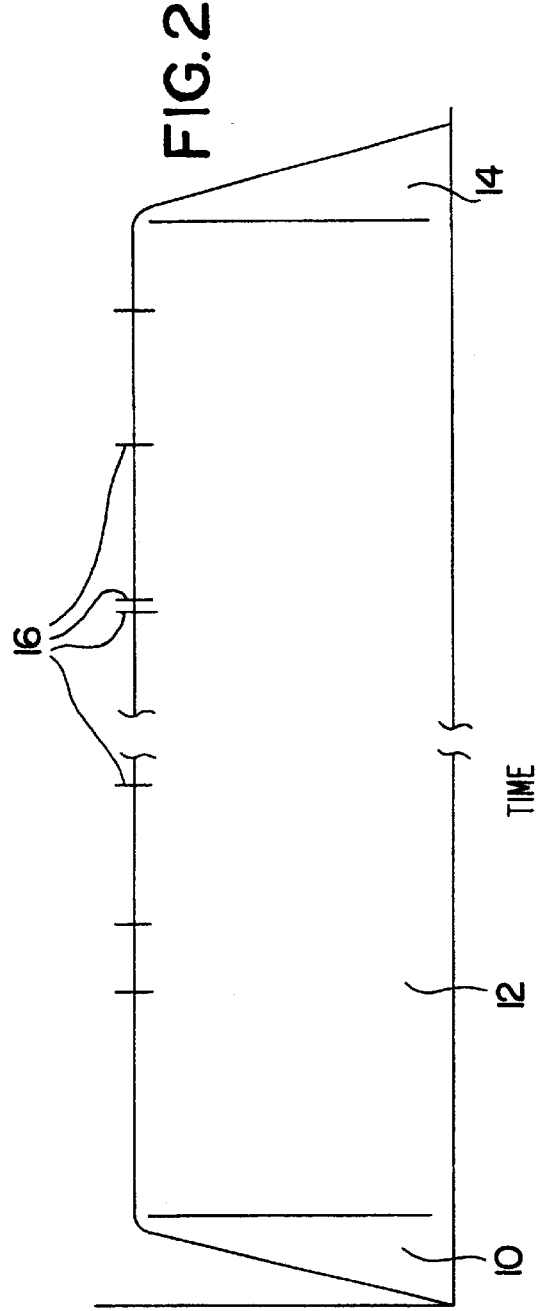

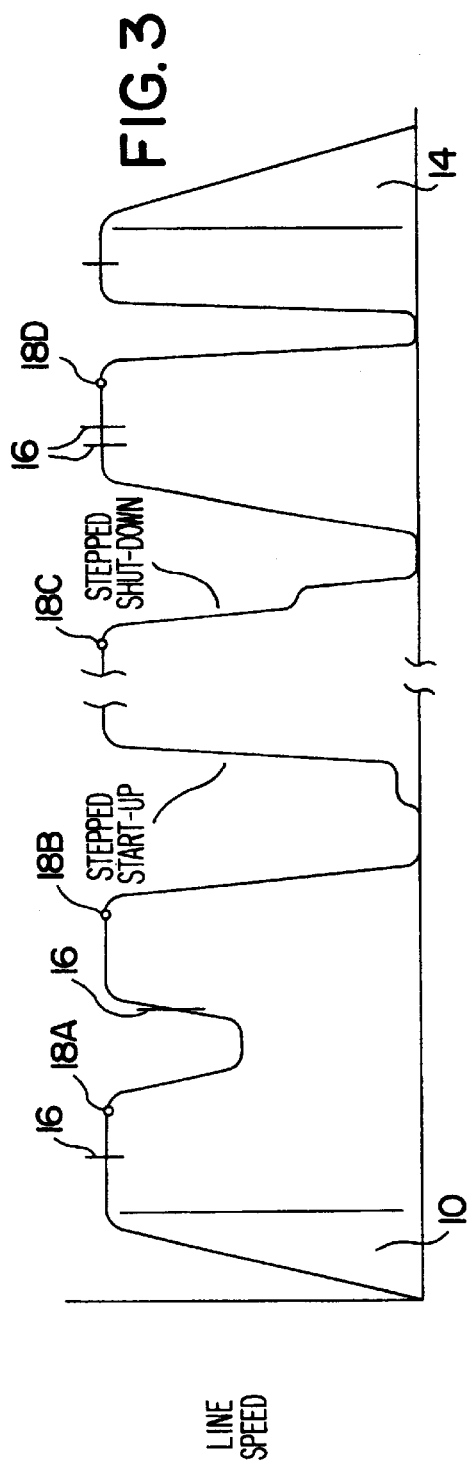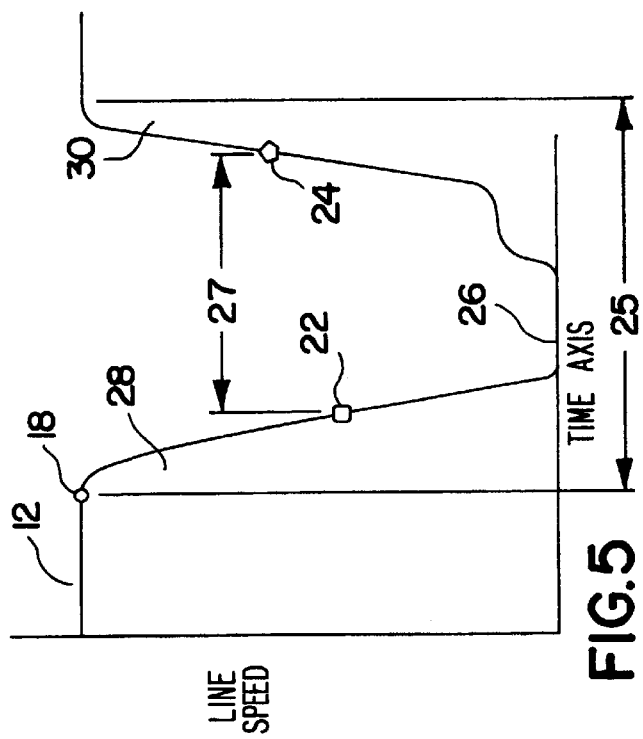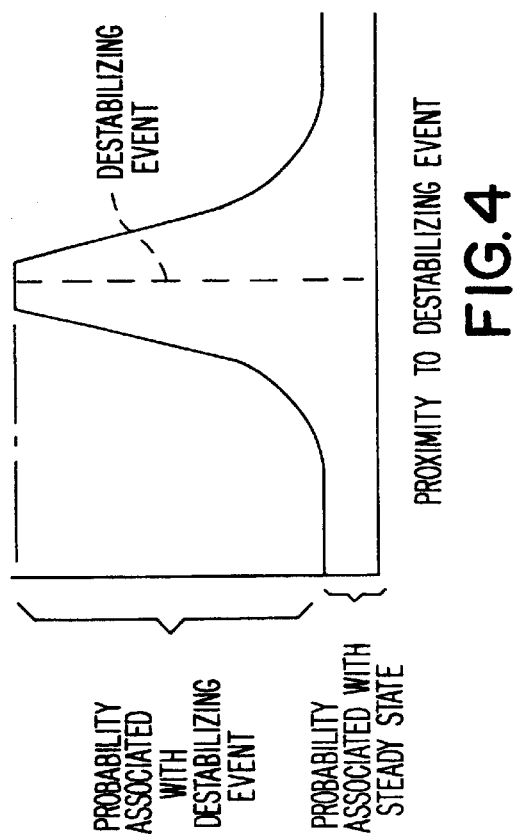

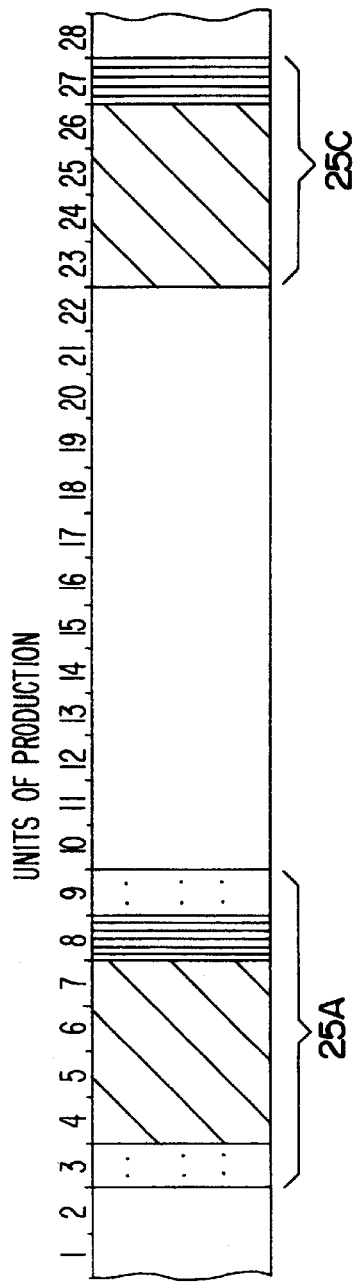
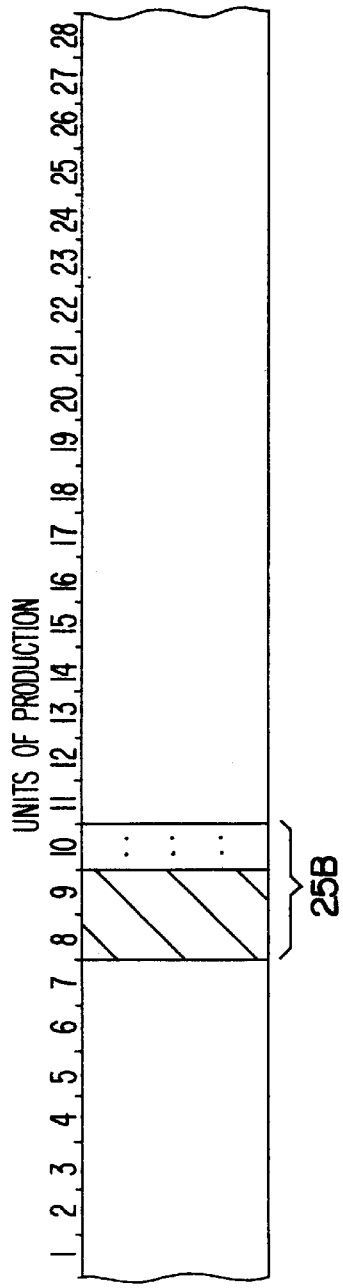
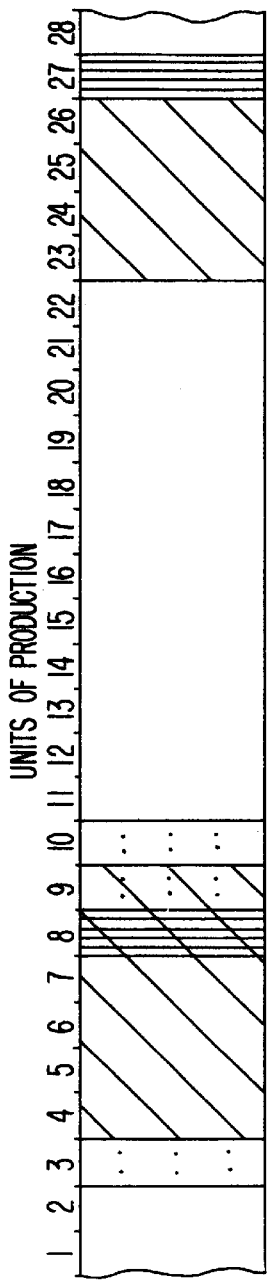

CONTROL MODEL

BACKGROUND

This invention relates to apparatus and methods for automatically monitoring and evaluating manufacturing processes, for example operations which produce an ongoing stream of outputs such as discrete absorbent articles effective to absorb body fluids, for example disposable diapers. Such absorbent article products are typically fabricated as a sequence of work pieces being continuously processed on a continuous web and/or continuous processing line. Such absorbent article product generally comprises an absorbent core confined between a moisture impervious baffle of e.g. polyethylene and a moisture pervious body side liner of e.g. non-woven fibrous material. The absorbent articles are typically made by advancing one of the webs along a longitudinally extending path, applying the absorbent core to a first one of the webs, and then applying the second web over the combination of the first web and the absorbent core. Other elements such as elastics, leg cuffs, containment flaps, waste bands, and the like are added as desired for the particular product being manufactured, either before, during, or after, applying the second web. Such elements may be oriented longitudinally along the path, or transverse to the path, or may be orientation neutral.

Typical such manufacturing processes are designed to operate at steady state at a pre-determined set of operating conditions. A typical such process has a beginning and an end, and has a start-up period corresponding with the beginning of the operation of the process, and a shut-down period corresponding with the end of the operation of the process. The start-up period of the operation generally extends from the initiation of the process to the time the process reaches specified steady state conditions. The shut-down period of the operation generally extends from the time the process leaves steady state conditions to the termination of operation of the process.

While the process is operating at steady state conditions, the result desired from the process is desirably and typically achieved. For example, where the process is designed to produce a certain manufactured good, acceptable manufactured goods are normally produced when the process is operating at specified steady state conditions.

As used herein, "steady state" conditions represents more than a single specific set of process conditions. Namely, "steady state" represents a range of specified process conditions which correspond with a high probability that acceptable goods will be produced, namely that the products produced will correspond with specified product parameters.

Known statistical models and control models are based on assumptions that the goods produced during operation of a given such process represent a single homogeneous population of goods. The focus of such statistical models and control models is based on steady state conditions.

However, actual operation of many manufacturing processes, including highly automated processes, typically includes the occurrence of periodic, and in some cases numerous, destabilizing events. A "destabilizing event" is any event which upsets, interferes with, or otherwise destabilizes the ongoing steady state characteristics of either process parameters or unit-to-unit product parameters. A typical such destabilizing event is one which either causes unacceptable product to be made, or which causes the process controller to detect and/or report an anomalous condition, or both.

Depending on the nature and severity of any given destabilizing event, the destabilizing event may lead to any one or more of a number of possible results, for example, shutting down of the operation, speeding up or slowing down of the operation, changing one or more of the other operating parameters, sounding of an alarm to alert an operator, or the like. Upon the occurrence of such destabilizing events, the products fabricated by such manufacturing operation may be moving out of the tolerance range of predetermined required specifications whereupon corrective action should be taken in the manufacturing operation; or the product stream may move outside such specifications and should be culled from the product stream.

A variety of possible events in the manufacturing operation can cause the production of absorbent articles which fall outside the specification range. For example, stretchable materials can be stretched less than, or more than, desired. Elements can become misaligned relative to correct registration in the manufacturing operation. Timing between process steps, or speed of advance of an element, can be slightly out-of-tolerance. If such non-catastrophic changes in process conditions can be detected quickly enough, typically process corrections can be made, and the variances from target conditions can accordingly be reduced, without having to shut down the manufacturing operation and without having to cull, and thereby waste, product.

Other destabilizing events require more drastic action. Typical such more drastic destabilizing events are splices in any of the several inputs being fed into the process, web breaks, defective zones in an input material, the start-up period, the shut-down period, and the like. Typical responses to such more drastic anomalous destabilizing events might be culling product from the output, sending one or more corrective control commands to control actuators on the process line, sounding an alarm, slowing down the processing line, shutting down the process line, and the like.

A variety of automatic product inspection systems are available for routine ongoing automatic inspection of product being produced on a manufacturing line and for periodically and automatically taking samples for back-up manual evaluation. Indeed, periodic manual inspection of product samples is still important as a final assurance that quality product is being produced. The question to be addressed in that regard is directed toward timing and frequency of sampling and corresponding manual inspection and evaluation.

Where product is outside the specification range, and should be culled, it is desired to cull all defective product, but only that product which is in fact defective. If too little product is culled, or if the wrong product is culled, then defective product is inappropriately released into the stream of commerce. On the other hand, if product which in fact meets product specification is culled, then acceptable product is being wasted.

Body fluid absorbing absorbent articles such as are of interest herein for implementation of the invention are typically manufactured at speeds of about 50 to about 1200 articles per minute on a given manufacturing line. Accordingly, it is impossible for an operator to manually inspect each and every article so produced. If the operator reacts conservatively, culling product every time he/she has a suspicion, but no solid evidence, that some product may not meet specification, then a significant amount of in fact good product will have been culled. By contrast, if the operator takes action only when a defect has been confirmed using visual or other manual inspection, defective product may already have been released into the stream of commerce before the defective condition is discovered.

One way for the operator to inspect the product for conformity with the specification range is for the operator to periodically gather and inspect, off-line, physical samples of the product being produced. Random such inspections stand little prospect of detecting temporary out-of-specification conditions or of identifying leading and/or trailing elements of a group of defective products being produced. Where such samples are taken by an operator in response to a suspected out-of-specification condition, given the high rate of speed at which such articles are manufactured, by the time the operator completes the inspection, the suspected offensive condition may have existed long enough that questionable or defective product will have either been shipped or culled without the operator having any solid basis on which to make the ship/cull decision. Further, automated manufacturing process controls may have self-corrected the defect condition before the operator can complete the visual inspection and act on the results of such visual inspection.

While off-line inspection can be a primary determinant of quality, and typically defines the final quality and disposition of the product, on-line inspection, and off-line inspection of on-line-collected data, typically associated with certain manufacturing events, may provide valuable insight into both the operational characteristics of the manufacturing process, and the final quality parameters of the product.

Thus, in processes that operate at speeds such that manual inspection of each unit of product is impossible, the primary mechanism for inspecting each unit of product is an automatic inspection and control system, backed up by periodic manual inspections to confirm the accuracy of the decisions being made by the automatic inspection and control systems.

Known statistical control models can be used for, among other things, determining when samples are to be taken from the processing line, and manually analyzed and evaluated for conformance with pre-determined specifications for the product so being produced. Known such control models indicate sampling at periods based on steady state operation.

The desired contributions of a statistical control model are (i) to provide one or more sets of conditions under which product is automatically culled in anticipation that most if not all defective product will be so rejected and (ii) to provide one or more sets of conditions under which samples are taken for back-up manual inspection.

The problem with known control models is that they are designed for and focused on fine-tuning steady state processes; and do not take into full account the additional factors which come into play when significant destabilizing events occur. Specifically, known control models are optimized for bringing an operating system back to a set of target operating conditions when the operating system has strayed from the target set of conditions. Namely, known control models are optimized for maintaining steady state conditions. Correspondingly, known control models are not designed to distinguish product made during numerous temporary destabilizing events in terms of the probability that such product may represent a second or third product population. Neither are such control models optimized for sampling product as a direct result of when a destabilizing event occurs.

As a result, while existing statistical control models may be rather efficient at identifying and culling defective product resulting from random or unpredictable anomalous conditions in the process, when the process has a destabilizing event, known statistical control models tend to ignore the probability that the portion of the product population which is associated with the destabilizing event could contain a larger than average number of defective units. Namely, the product which is passed on for shipping may contain too many defective units, and the product which is rejected, culled, may contain an undesirably high fraction of good product which should have gone to shipping instead of being rejected or culled for disposal or recycling.

It is an object of the invention to provide methods for setting up and controlling a process, for example using a statistical control model, which provides for bringing the operating system to a set of target operating conditions assuming at least first and second product population segments, and corresponding first and second sets of assumptions about the respective product population segments, and the process steps to be taken to optimize process quality and efficiency, and corresponding product quality and efficiency.

It is another object to provide first and second control model segments, based on separate product population assumptions, or operating condition assumptions, for the respective first and second product population segments.

It is still another object to provide first and second separate and distinct sampling methods corresponding to the first and second product population segments.

It is a further object to provide first sampling methods for taking quality-check samples during steady state operation, and second different and distinct sampling methods for taking quality-check samples before, during, and after destabilizing events until such time as the process has been restored substantially to steady state conditions, or to conditions where acceptable product is being otherwise reliably produced.

It is yet another object to provide novel and improved statistical control model for controlling processes.

A still further object is to provide output populations, for example product populations, having improved levels of conformity with output specifications, without a significant increase in the amount of actually acceptable product which is in fact rejected by the automatic inspection and control system.

It is yet another object to provide product sampling and inspection methods which identify desirable changes to the automatic ship/cull decision settings of the automatic inspection, control, and cull system, which result in the automatic system better distinguishing actually acceptable output from actually defective output.

SUMMARY

This invention contemplates a method of controlling a process having operating conditions, one or more inputs, and one or more outputs, and wherein the process defines parameters of the one or more outputs. The method comprises defining a first steady state set of first respective ones of the operating conditions representing one or more acceptable operating parameters of the process, and target operating parameters included therein. The method further comprises defining a second steady state set of output conditions representing previously-defined acceptable parameters of the one or more outputs, and target output parameters included therein. The method still further comprises operating the process, and routinely sampling output on the basis of a single output population model, detecting destabilizing process events which result in output not representing acceptable output parameters, defining one or more third sets of operating conditions according to which output is rejected and/or defining one or more fourth sets of output parameters according to which output is rejected. Upon detecting a destabilizing process event, the method temporarily implements sampling assuming a dual population output, including automatically rejecting output whenever any one of either the operating conditions or the output parameters is violated, thereby establishing a leading automatic output rejection and a trailing automatic output rejection, and thus defining an automatic output rejection period according to which output is automatically rejected in response to the destabilizing event. The method also defines a leading transition period proximate and before the automatic output rejection period, and a trailing transition period proximate and after the automatic output rejection period. The transition periods, overall, representing periods of higher than average risk that output will be defective. The method automatically identifies, and optionally measures and/or manages samples and/or measures, segregates, or otherwise manages output in at least one of the leading transition period and the trailing transition period, as well as correcting the process in accord with the respective destabilizing event or events.

The method preferably includes returning to routinely sampling output based on a single output population model focused on typical steady state operation when both the operating parameters and output conditions have indicated the existence of acceptable specified steady state conditions, and no new destabilizing event has been detected.

The method further preferably includes automatically sampling output from both the leading transition period and the trailing transition period.

The method further contemplates evaluating the sampled transition period output against previously-specified acceptable output parameters and making reject/accept decisions based on such evaluations.

The method preferably includes, when transition period output is rejected, further sampling and manually evaluating output which is farther away, chronologically in time, respectively before or after, the automatic rejection period.

Preferred methods include manually evaluating sampled transition period output against previously-specified acceptable output parameters and making adjustments to the process based on such evaluation.

Some embodiments include operating the process at steady state conditions within the specified acceptable parameters at least one of before a leading transition period or after a trailing transition period, and defining a respective beginning or end of the respective transition period away from the automatic output rejection period.

Some sophisticated embodiments of the invention include compiling and evaluating data representing numerous ones of the transition periods and thereby developing desirable adjustments to a length of at least one of the transition periods and correspondingly adjusting the respective transition period in which samples are to be automatically collected, and wherein the adjustment of the respective transition period preferably results in an improved balance between actual accept/reject decisions and the actual acceptability of the output based on the acceptable output parameters.

Routine sampling, outside the destabilizing event windows may be based on steady state operating speeds while event driven sampling is based on and/or triggered by the occurrence of destabilizing events. The detected destabilizing events may comprise events which have little or no direct affect on operating speed of the process, or can comprise events which have substantial direct affect on operating speed of the process, or both, including shutting the process down.

The invention further contemplates embodiments comprising a method of controlling a process having operating conditions, one or more inputs, and one or more outputs. The process defines parameters of the one or more outputs. The method comprises defining a first steady state set of first respective ones of the operating conditions representing one or more previously-specified acceptable operating parameters of the process; defining a second steady state set of output conditions representing acceptable parameters of the one or more outputs; operating and controlling the process, and routinely sampling output on the basis of (i) a first output population segment produced under substantially steady state conditions and (ii) at least a second output population segment produced pursuant to destabilizing process events; routinely sampling output on the basis of steady state operation during steady state operation; detecting destabilizing process events which result in output not representing acceptable output parameters; defining one or more third sets of operating conditions according to which output is rejected and/or defining one or more fourth sets of output parameters according to which output is rejected; upon detecting a destabilizing process event in step (e), temporarily implementing output identification, and operations management, on the basis of the population segment typically produced pursuant to the respective type of extant destabilizing process event; and when both operating parameters and output conditions indicate existence of acceptable steady state condition, and no new destabilizing event has been detected, returning to sampling output on the basis of steady state operation.

The invention yet further contemplates embodiments comprising a statistical control model for controlling a process having operating conditions, one or more inputs, and one or more outputs, and wherein the process defines parameters of the one or more outputs. The statistical control model comprises defining a first steady state set of first respective ones of the operating conditions representing one or more acceptable operating parameters of the process, and target operating parameters included therein. The statistical control model further comprises defining a second steady state set of output conditions representing acceptable parameters of the one or more outputs, and target output parameters included therein. The statistical control model further comprises operating the process, and routinely sampling output on the basis of a single output population model, detecting destabilizing process events which result in output not representing acceptable output parameters, defining one or more third sets of operating conditions according to which output is rejected and/or defining one or more fourth sets of output parameters according to which output is rejected. Upon detecting a destabilizing process event, the statistical control model temporarily implements sampling assuming a dual population output, including automatically rejecting output whenever any one of either the operating conditions or the output parameters is violated, thereby establishing a leading automatic output rejection and a trailing automatic output rejection, and thus defining an automatic output rejection period according to which output is automatically rejected in response to the destabilizing event. The statistical control model also defines a leading transition period proximate and before the automatic output rejection period, and a trailing transition period proximate and after the automatic output rejection period. The transition periods, overall, represent periods of higher than average risk that output will be defective. The statistical control model automatically samples output in at least one of the leading transition period and the trailing transition period.

The invention yet further comprehends a multiple-segment product population, comprising a not-culled population segment having predominantly acceptable members of the population, and a culled population segment having a steady state cull element, an automatic cull segment, and a transition inspection cull segment. The culled population segment represents defining a first steady state set of operating conditions representing one or more acceptable operating parameters, and target operating parameters included therein. The multiple-segment product population further represents defining a second steady state set of output conditions representing acceptable output parameters, and target output parameters included therein. The multiple-segment product population further comprises routinely sampling output on the basis of a single output population model, detecting destabilizing events which result in output not representing acceptable output, defining one or more third sets of operating conditions according to which output is culled and/or defining one or more fourth sets of output parameters according to which output is culled. Upon detecting a destabilizing event, sampling is temporarily implemented according to a multiple population output, including automatically rejecting output whenever any one of either the operating conditions or the output parameters are violated, thereby establishing a leading automatic output cull and a trailing automatic output cull, and thus defining an automatic output cull period according to which output is automatically culled in response to the destabilizing event. The multiple-segment product population further represents defining a leading transition period proximate and before the automatic output rejection period, and a trailing transition period proximate and after the automatic output rejection period. The transition periods, overall, represent periods of higher than average risk that output will be defective. The multiple-segment product population still further represents automatic sampling of the output in at least one of the leading transition period and the trailing transition period.

BRIEF DESCRIPTION OF THE DRAWINGS

FIG. 1 is a graph illustrating the degree of achievement of specified steady state conditions.

FIG. 2 is a graph illustrating the degree of achievement of specified steady state conditions as in FIG. 1, but includes destabilizing events that can occur, even during purportedly steady state operation.

FIG. 3 is a graph illustrating the degree of achievement of specified steady state conditions, including destabilizing events that have little or no affect on line speed, as well as destabilizing events which do have significant affect on line speed.

FIG. 4 is a graph illustrating that when a destabilizing event occurs, the probability of the process producing defective output is related to a combination of the probability associated with steady state and the probability associated with the proximity of the respective output in question to the destabilizing event.

FIG. 5 is an enlarged portion of a graph illustrating detail of response of a process upon the occurrence of a destabilizing event which significantly affects the speed of the process.

FIGS. 6A, 6B, and 6C illustrate the result of cull actions based on the combination of process-initiated responses and product-inspection-initiated responses.

Figure 7:
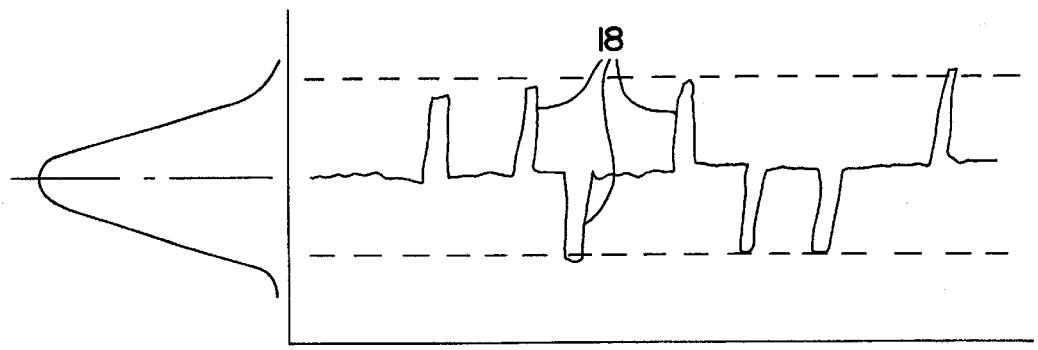
FIG. 7 illustrates a control model based on a single output population.

The invention is not limited in its application to the details of construction or the arrangement of the components set forth in the following description or illustrated in the drawings. The invention is capable of other embodiments or of being practiced or carried out in other various ways. Also, it is to be understood that the terminology and phraseology employed herein is for purpose of description and illustration and should not be regarded as limiting. Like reference numerals are used to indicate like components.

DESCRIPTION OF THE ILLUSTRATED EMBODIMENTS

A discrepancy appears to exist between integrated control automatic inspection and quality control system estimates of outgoing rates of quality defects and off-line system integrity checks of defects. The apparent discrepancy tends to under-estimate the defect rate relative to that which is found by off-line quality validation. This fact, in combination with the difficulty of organizing and coordinating widespread process optimization efforts speaks to the difficulty associated with effective identification of specific issues for engineering process improvements. Namely, the information produced by known automatic inspection and quality control systems is insufficient to provide direction for effective process improvement activity, whether such improvement be directed toward the steady state condition or the destabilizing condition.

Strategic methods are disclosed for generating information required to permit definition of quality improvement activity, and to permit effective long term monitoring of process performance thereafter.

Improving outgoing quality level is assumed to be a primary path to improving product performance and customer satisfaction, and consequently for improving productivity in terms of efficiency and yield.

The defect allocation model of the invention departs from current statistical process control theory and applications utilized in integrated control by defining the contemplated converting process as a mathematical combination of product populations that are defined according to the specific state of the process at the time of manufacture of a specific unit of product.

Thus, the defect allocation model of the invention is in contrast to the assumption of randomly sampled units from a homogeneous population that is sometimes upset by special causes. Accordingly, under the allocation model of the invention, each unit of product is classified into at least one of two or more segments of the population, which segments are identified with the state of the process at that specific point in time, such that a steady state population segment exists as well as one or more upset event population segments.

The product population segments can be further summarized into one of at least three primary classes, namely culled, not culled destabilizing event, not culled steady state. These categories permit more nearly accurate definition of, respectively, auto-culled product, upset event steady state product, samples per steady state assumptions, and transition/stress product, and samples per stress/transition assumptions. These categories further facilitate more nearly accurate definition of events and conditions, affecting outgoing quality levels by providing for evaluation of product variation against the classification structure defining the respective population segments. Thus, the specific manufacturing circumstances that impact product consistency and outgoing quality levels are identified to specific units of product. This facilitates derivation of the outgoing quality level, as rate of defective units in parts per million as the summation of events occurring during any specified period of production and identification of specific units of product with respective such events. This approach is fundamentally different from current statistical process control doctrine in that the unit-based production is now linked to specific manufacturing conditions that are responsible for generating variations beyond the level nominal to the operation under conditions of steady state operation.

Referring now to the drawings, FIG. 1 is a graph illustrating the degree of achievement of specified steady state conditions, either process conditions or product properties, in a manufacturing process. The degree of achievement of the desired conditions is illustrated with respect to time. In FIG. 1, the upright axis represents a collection of parameters, namely the product specification, which must be achieved in order for the product to be acceptable. While the upright axis does include line speed in FIG. 1, other parameters are also included. Thus, any break in steady state conditions in FIG. 1 can represent a change in any one of the required conditions, and may or may not indicate a change in line speed of the manufacturing operation.

FIG. 1 illustrates a beginning start-up period 10, a following intermediate period 12 of steady state operation, and a subsequent shut-down period 14. While off-specification output may be produced during the start-up period, the start-up period is illustrated as being relatively short and thus the amount of cull material produced during the start-up period is comparatively quite small.

Following start-up, the process operates at steady state, constantly producing a high fraction of acceptable quality product until a planned shut-down period. Still referring to FIG. 1, while off-specification output may be produced during the time required for planned shut-down, the shut-down period is again illustrated as being relatively short and thus the amount of off-specification material produced during the planned shut-down period is comparatively quite small. Between the start-up and shut-down periods, the process, assuming the process is well designed, produces quality product at a highly advantageous rate, whereby production, and therefore profits, may be maximized.

It should be understood that FIG. 1 represents an idealized manufacturing condition, which is often not realized in real-world manufacturing environments. Rather, real-world manufacturing environments often include destabilizing events, whether planned or unplanned, which cause the output of the process to fall outside the product specifications; and whereby such off-specification product should be rejected and/or culled.

FIG. 2 represents a manufacturing process as in FIG. 1, but introduces the concept that destabilizing events can and do often occur during operation of the manufacturing process, even during purportedly steady state operation. Such destabilizing events can affect any one or more of a wide range of the parameters specified for the product. Depending which parameter or parameters are affected, the manufacturing process may or may not be shut down. Where the expectation is that the anomalous condition will be corrected in an acceptably short period of time, the operation typically continues and rejects or culls product as necessary to preserve the level of quality of the product being shipped Where the anomaly is not likely to be corrected without shut-down, or where correction will take considerable time, then a shut-down is preferred. The length of time during which the manufacturing operation remains shut down depends on how long it takes to correct for the anomaly. FIG. 2 represents the situation wherein the anomaly is corrected in a short period of time, for example no more than a few seconds, whereby the process can and should continue operating and acceptable product is again being produced within a short period of time.

The destabilizing events 16 depicted in FIG. 2 on, for example, a manufacturing operation for making absorbent articles for absorbing human exudates, and which have little or no affect on process line speed, can be representative of, for example, splices, a web wandering from a specified track centerline, light-weight in-feed material, heavy-weight in-feed material, drive speed inconsistencies, misapplied product elements, and the like. Generally, the destabilizing events 16 depicted in FIG. 2 have little or no affect on the line speed of the manufacturing operation.

FIG. 3 is like FIGS. 1 and 2 in its representation of an initial start-up period 10 and a planned shut-down period 14. FIG. 3 is like FIG. 2 in its representation of destabilizing events 16 that have little or no affect on line speed. FIG. 3 shows, in addition, a series of four destabilizing events 18A, 18B, 18C, and 18D, which do have significant affects on line speed, and wherein events 18B, 18C, and 18D result in the process line being temporarily shut down. Unless plans are changed during operation of the process, the initiation of planned routine terminal shut-down 14 is independent of the operation/existence of any otherwise destabilizing event.

FIG. 4 illustrates a significant discovery of the invention. Namely applicants have discovered that when a destabilizing event 16 or 18 occurs, the probability of the process producing defective output material is related not only to a statistical steady state sampling model, but also to the proximity of the respective output in question to the destabilizing event, whether in time or distance, or both. FIG. 4 represents a composite of time and distance as a general indication of the relationship between proximity to the destabilizing event and the likelihood that a particular unit of product will be defective.

As seen in FIG. 4, a product unit closely adjacent the destabilizing event has a relatively higher probability of being out of specification, and the farther away from the destabilizing event is the unit of product being analyzed, the lower the probability that the unit of product will have been deleteriously affected by the destabilizing event such that defective product might be produced.

Units of product produced remote from the destabilizing event in time and distance have a low probability of being adversely affected by the destabilizing event, whereby the probability of such unit of product being defective is related primarily to the probabilities associated with steady state conditions. Closer to the destabilizing event, the probability of the unit of product being defective is a combination of (i) the low probability of defect associated with steady state operation and (ii) the respective probability of defect associated with the destabilizing event. In some cases, for example a splice, the probability of producing at least one unit of defective material approaches 100 percent.

While commercially available statistical control models assume a single homogeneous population of the output of the process, having a generally uniform continuum of properties of the output population, in view of the above analysis of FIGS. 1–3, and the resulting discovery illustrated in FIG. 4, applicants propose that a more realistic representation of the population of outputs being produced by a representative manufacturing process in fact has at least two distinct and separately identifiable population segments. The first segment is that produced under steady state conditions, such as those illustrated in FIG. 1. The second segment is that produced under the stress conditions associated with any one or more destabilizing events.

Applicants have discovered that, when a conventional statistical control model is used to control, cull, and sample, the manufacture of absorbent articles, of the actually defective product which is released for shipping, an inordinate amount of such defective product represents product which was produced in transition zones 28, 30. Thus, efforts at better distinguishing defective product from acceptable product may well be focused on transition zones 28, 30.

Since the overall population of units produced represents two or more separately identifiable population segments, applicants propose that the statistical control model, used for automatically controlling production, sampling, culling, and the like, of units of product, should be adjusted so as to reflect a typical steady state control model only during existence of steady state conditions.

Accordingly, in the invention, for the remainder of the time, namely during stress periods, the control model used for automatically controlling production, sampling, culling, and the like, of units of product, reflects the increased risk of producing defective, off-specification product proximate a destabilizing event.

The inventors' overall control model thus comprises first and second control model elements. The first control model element assumes steady state conditions, and controls production, samples, and automatic product culling on the basis of steady state assumptions. The second control model element assumes the stress conditions in transition zones 28, 30, and controls production, samples, automatic product culling, and the like, on the basis of the stress conditions assumptions.

We turn now to FIG. 5 for a more detailed analysis of some of the steps in the methods of controlling a manufacturing operation such as the typical operation illustrated in FIG. 3. Further, for the sake of general illustration, the upstanding axis of FIG. 5 represents a collection of hereunnamed parameters which must be met in order for the respective process to be defined as operating within specification. It should be understood that FIG. 5 illustrates only a short time segment of a manufacturing process having a period of operation longer than the time segment illustrated in FIG. 5.

Operation of the invention does not depend on naming any one set of parameters, or any one type of process. The actual identity of the parameters is not important for this general discussion. Rather, the invention can be fully understood without naming specific parameters. For implementation of the invention herein, it is, of course, important to identify the specific parameters to be monitored and controlled.

Turning now to the specifics of FIG. 5, intermediate period 12 of steady state operation is illustrated generally on opposing sides of a destabilizing event 18 which results in temporary shut-down of the process. Upon occurrence of the destabilizing event, product being processed by the process is subjected to an abnormal stress condition which, at some point into the progress of the shut-down, results in production of off-specification product which should be culled.

Likewise, when the process is started back up after the temporary shut-down, the initial units of material being produced are off-specification and should be culled; and at some point into the progress of the start-up, the product being produced is again within acceptable specification, and should be released for shipping.

In view of the speed at which manufacturing lines operate, for example up to about 1200 or more units per minute in the absorbent article art, it is impossible for a human operator to physically inspect each and every unit of product coming off the production line in order to determine the exact times of transition from acceptable product to defective product, and from defective product to acceptable product. Accordingly, it is common practice to implement automatic inspection, control, and culling systems, including process control apparatus, culling apparatus, and control and culling procedures for such manufacturing operations.

Such systems can provide substantial operational control of the manufacturing process, including inspecting each unit of product according to a limited set of parameters, developing and implementing process control adjustments to the operation, and culling action according to certain process parameters and product parameters. For example, known systems may be set up to cull product when the process speed is reduced to a specified rate, or to stop culling when the process speed is increased to a specified rate. The inspection system can also be set up to cull a certain number of product units upon the occurrence of a predetermined event such as a splice passing through the processing line. Further, the inspection system can be set up to cull product any time product parameters fall outside pre-set limits for certain data measurements which are being automatically made on product. Similarly, the control system can physically separate the output into a first population segment representing steady state operation and a second population segment representing operation under destabilizing event conditions. The first such population segment generally has a relatively lower incidence of out-of-tolerance product. The second such population segment generally has a relatively higher incidence of out-of-tolerance product.

Known such systems are based on steady state operation. This invention is concerned with the proper classification of product into either the cull category or the not-cull category. While such automatic inspection systems can respond in a predetermined manner by culling product in response to certain destabilizing events, known set-ups for such actions are based on global understanding, for example an engineer's understanding, of the process, and of what amount, if any, of product needs to be culled when certain destabilizing events occur.

The degree of success or failure of the inspection system, in properly culling defective product, while not culling product which is actually acceptable product, depends on the ability of the inspection system to distinguish between product which is actually acceptable and product which is actually defective. While known automatic control, inspection and culling systems provide substantial capability for controlling the release of defective material, any instruction set which will absolutely separate out all defective material normally also separates out a significant amount of material which is not actually defective.

The objects of this invention are directed toward better distinguishing material which is actually defective from material which is actually acceptable. Namely, this invention is directed toward reducing the amount of actually acceptable product which is rejected and culled, and reducing the amount of actually defective product which is released for shipping into the stream of commerce.

In an automatic inspection, control, and cull system, the system responds to certain process parameters. For example, when line speed is reduced to a first certain predetermined minimum speed, all subsequent product is culled, until the speed again increases to a second certain predetermined minimum speed, which may or may not be the same as the speed at which culling was initiated. Certain product parameters may also be automatically inspected, and corrective action, or culling action, or both, may be taken according to the results of such inspections.

FIG. 5 illustrates a single destabilizing event 18 which affects line speed, and the relationships between line speed, time, and culling action, which are related to the destabilizing event. While the destabilizing event 18 is depicted at a single point in time, the destabilizing event may well be an ongoing action for a significant portion of the destabilizing event window 25.

As soon as the destabilizing event occurs at 18, line speed begins to drop. According to known inspection and culling systems, a normal set of predetermined control conditions would be set such that, when the line speed was reduced to a specified trigger level, such as at trigger event 22, the inspection and control system automatically begins to cull product, and continues to automatically cull product until such time as the speed increases to a second trigger level 24, or until a specified number of units of product have been processed, whereupon automatic culling is discontinued.

A first assumption in the automatic culling operation is that the person who specified the parameters of trigger events 22, 24 had exact knowledge of when the process would begin to produce defective product, and when the process would stop producing defective product. Second, the automatic culling assumes that the manufacturing system will begin producing defective product at the same values of the parameters every time the specified triggering event 22 occurs, and will cease producing defective product every time the parameter is restored to the second triggerlevel at 24. Third, the automatic culling assumes that each destabilizing event occurs under precisely the same set of operating conditions, whereby the process will respond in exactly the same manner. Fourth, automatic culling assumes that a given set of machinery comprising a manufacturing line performs the same as an apparently identical second manufacturing line.

Real life experience, of course, indicates that a wide variety of parameters are often in effect in many operations, whether manufacturing-related operations, operations related to methods of doing business, or service-related operations. Accordingly, in order to conservatively prevent release of defective product, the person setting up the control and cull parameters for the automatic control and culling system may instruct the system to begin culling product shortly after the speed begins to fall, and to keep culling product until the speed has been restored to nearly steady state, respectively higher on the curve of FIG. 5 than are shown for trigger events 22 and 24. This truly conservative approach culls relatively more product which is not actually defective.

As an alternative, the person setting up the control and cull parameters for the automatic control and culling system may instruct the system to begin culling product only after the speed has fallen off farther, for example more than shown for trigger event 22, and to stop culling early upon the speed beginning to increase, for example before the time shown in FIG. 5 for trigger event 24. This more aggressive approach releases to shipping a significant amount of product which is actually defective.

The difficulty for the person setting up the inspection, control, and cull instructions for the automatic system is to know where to set the automatic triggers such as 22 and 24 such that no more than a minimum amount of good product is culled, and no more than a minimum amount of defective product is released for shipping. The problem is further compounded by the fact that the entire set of events relating to the destabilizing event, including initiation at 18, beginning of culling at 22, full shut down as at 26, termination of culling at 24, and restoration of the process to steady state conditions, can all take place in less than a second, or up to several seconds. The automatic rejection period 27, which exists between trigger event 22 and trigger event 24, represents a respectively shorter period, allowing for the times defined by transition zones 28, 30.

Typically, the entire set of events takes no more than a few seconds, though longer periods are fully comprehended by, and are compatible with, the sampling and control discoveries of the invention.

Thus, while the destabilizing events occur too fast, and process conditions during destabilizing events change too fast, for effective human intervention to control the process, there is a need to better control such processes in order to better distinguish actually acceptable product from defective product.

The first real issue is to determine the point, for example during start-up or restart-up, whether planned start-up or shut-down or such event coupled with a destabilizing event, when the process first starts producing acceptable product. As soon as the process begins producing acceptable product, product disposition should be transferred from cull to ship. The second real issue is to determine the point, for example during shut down, or ramp down for a destabilizing event, when the process first starts producing off-specification, non-acceptable product. As soon as the process begins producing non-acceptable product, product disposition should be transferred from ship to cull.

If automatic triggers 22 and 24 have been properly selected, point 22 will separate acceptable product from non-acceptable product, and point 24 will separate non-acceptable product from acceptable product. To the extent points 22 and/or 24 are improperly positioned, defective product may be improperly shipped and/or acceptable product may be improperly culled.

The invention thus contemplates taking additional samples of the product or other output where the output is under atypical stress, namely around destabilizing events, in order to better define the boundary between production of acceptable product and production of defective product. Namely, when the process experiences a destabilizing event, the occurrence of the destabilizing event triggers a taking of samples according to a sequence related to the timing and extent of the destabilizing event. Where automatic culling is so set up for correlation to a destabilizing type event such as the destabilizing event represented by 18, a product sample is automatically taken immediately before the first product unit that is to be automatically culled as defective, namely immediately ahead of trigger event 22. A manual evaluation of the sample is then conducted as a back-up to the automatic decision regarding when to automatically cull product.

Similarly, after the specified number of units of product have been culled, or when the process, or product parameters, achieve a specified level of recovery from the destabilizing event, whichever is last, the control system automatically begins processing the succeeding units of product for shipment. As with the beginning of culling, the first such unit that is released for shipping is automatically sampled and the sample is manually evaluated as a back-up to the automatic decision of the control system regarding when to automatically begin shipping product.

If such sampling confirms that a sufficient amount of product is being culled to account for the destabilizing event, the next question is whether any of the culled product is actually acceptable material whereby good product is being culled. That question is answered by instructing the control system to automatically take as a sample the first unit of product after the beginning of automatic cull (after event 22), and the last unit of product before the ending of automatic cull (before event 24). Such samples can be taken in place of the above described sampling before event 22 and after event 24, or in addition to such sampling.

To the extent the sampling confirms that triggers 22 and 24 are properly positioned, the process set-up is left unchanged. To the extent the sampling confirms that one or both of triggers 22 and 24 are improperly positioned, the trigger events are moved along the process curve to adjust the process such that the trigger events are properly placed. For example, if good product is discovered after trigger 22, then trigger 22 is moved, on e.g. FIG. 5, to the right in order to provide for shipping of additional good product during subsequent destabilizing events of the same type of identity. For example, if speed is the triggering event during shutdown, and good product is found after the triggering speed has been reached as at 22, then the process control is adjusted to begin culling at a slower triggering speed, whereby respective additional quantities of good product will have been shipped during subsequent similar shutdowns before culling begins, raising overall efficiency of the operation.

The time between the destabilizing event e.g. 18 and the restoration of steady state conditions is what is referred to herein as the destabilizing event window 25. The time during destabilizing event window 25, after initiation of the destabilizing event and before the beginning of automatic culling, is the lead transition period. The time during the destabilizing event window, after the end of automatic culling and before steady state is re-establishment, is the trailing transition period. The samples referred to above are generally taken during or proximate one or both of the transition periods. To the extent the samples indicate that trigger events 22 and/or 24 are improperly positioned along the time axis of the process, the trigger events are moved for subsequent use of the process, by so instructing the controller.

While the above description of sampling has been related to destabilizing events which have significant affect on line speed of the process, similar sampling and adjustments apply as well to destabilizing events which have little or no affect on line speed of the process. For example, splices generally do not require any change in line speed, though some number of units of product are typically culled. The question is how many units of product should be culled. The answer is obtained by sampling specifically those units of product immediately before and/or after the beginning and/ or ending of the established automatic culling practice.

When transition period product from immediately adjacent trigger event 22 or 24 is rejected, additional samples are preferably taken from product which is farther away, chronologically in time or by number of units of product, respectively before or after, automatic rejection period 27. Preferably, additional samples are taken progressively farther away from the automatic rejection period until such time as the sampled output meets acceptable output parameters whereupon, after confirming iterations of such data, the respective beginning or end of automatic rejection period 27 is accordingly adjusted along the time line.

As indicated above, when the process is operating at steady state conditions, sampling is conducted under a first set of steady state-related assumptions and according to known statistical sampling models that rely on steady state conditions. When a destabilizing event occurs, the sampling program converts to sampling according to a second set of the above real-time conditions, namely on the assumption that steady state conditions do not exist. The sampling program again reverts to the first set of steady state assumptions when steady state conditions are again approached and/or reached.

Thus, the sampling program operates on the assumption of two quite different sets of operating conditions. The first set of operating conditions is a set of steady state operating conditions. Product produced under this first set of steady state conditions has a relatively low risk of containing defective units of product, and is accordingly sampled according to steady state assumptions.

The second set of operating conditions represents destabilizing events as illustrated in e.g. FIGS. 2, 3, and 5. Output of the second set of operating conditions has a relatively high risk of containing defective units of product. For that reason, a high fraction of the product produced under this second set of operating conditions is automatically culled, and sampling is specifically taken at or proximate the trigger points in the transition zones. The first transition zone 28 is that period between the destabilizing event e.g. 18 and the cull trigger event 22. The second transition zone 30 is that period between the second trigger event 24 and resumption of steady state conditions.

While the parameter profile of a destabilizing event, namely the graphs of FIGS. 1–3 and 5, is not generally affected by the sampling specified in the invention, the placement of trigger events 22 and 24 along that profile can be, and is, adjusted based on the results of evaluating the samples so taken, such that the automatic cull triggers are better positioned to properly distinguish acceptable product from defective product. In addition, recognition of the destabilizing events and their impact on the resultant product quality provides direction for engineering changes which may be effective to adjust the process, to thereby reduce the frequency and/or severity of destabilizing events as well as to better control steady state operation.

In addition to the automatic event triggers 22 and 24, and the automatic sampling process described above, the automatic control system may automatically take a limited number of data measurements on each unit of product traversing the manufacturing line, or on a specified fraction of the units of such product. To the extent the automatic data measurements identify defective product, such defective product is automatically culled based on the measured defects, whether or not a destabilizing event has been detected and whether or not automatic culling is in effect based on process conditions. Optionally, upon the occurrence of such product-data-based culling, samples may be automatically collected for manual verification.

FIGS. 6A, 6B, and 6C represent the combined effect of controlling culling of product according to the combination of automatic culling based on process conditions and automatic culling based on measured product data. FIG. 6A represents accept/cull decisions of the automatic control system for 28 units of product, based on the combination of process conditions and automatically measured product parameters. Referring to FIG. 6A, a first destabilizing event window 25A exists during the period when units 3–9 are passing through the so-destabilized portion of the operating system. As indicated, units 4–7 are automatically culled because of process conditions, and unit 8 is culled because of at least one defective measured property automatically measured by the control system.

A second overlapping destabilizing event, illustrated in FIG. 6B, establishes a second destabilizing event window 25B for the period when units 7–10 are passing through the so-destabilized portion of the operating system. As indicated, units 8 and 9 are automatically culled because of process conditions. No units are culled, according to window 25B, because of product measurements.

A third destabilizing event, illustrated in FIG. 6A, establishes a third destabilizing event window 25C for the period when units 23–27 are passing through the so-established portion of the operating system. As indicated in FIG. 6A, units 23–26 are automatically culled because of process conditions. Unit 27 is culled because of defective product measurements automatically taken by the control system.

It should be understood that FIGS. 6A and 6B represent different aspects of the same time period in the same processing operation. FIG. 6C represents the composite result of overlapping the events of FIGS. 6A and 68 onto each other. As seen in FIG. 6C, units 4–7, 9, and 23–26, are automatically culled because of process conditions. Unit 27 is automatically culled because of defective product measurements automatically taken by the control system. Unit 8 is automatically culled because of both process conditions and defective product measurements automatically taken by the control system. While unit 8 is culled because of two separate factors, the illustrated example is premised on the assumption that either factor, operating alone, would be sufficient to affect the automatic culling of unit 8. Similarly, the cull decision could well be based on a combination of factors.

While the transition zones have been described in terms of destabilizing events, routine start-up corresponds generally to, and is treated like, a transition zone 30. Similarly, routine shut-down corresponds generally to, and is treated like, a transition zone 28.

As referred to herein, automatic collection of samples means that the process control automatically directs and effects the separation of the respective sample or samples out of the production line and the setting aside of such samples for manual evaluation.

The dual sampling mechanism of this invention focuses an increased amount of sampling energy on those periods of the operation of the process when the process is under abnormal stress, namely on transition zones 28, 30. This dual sampling takes into account the inventors' discovery that, of that portion of the shipped product which is actually defective, an inordinate fraction of that defective product was produced during a period within a destabilizing event window whereby focusing quality control efforts on the product produced during the destabilizing event window has a high prospect of improving the ability to properly distinguish acceptable product from defective product, as well as to adjust process parameters.

As referred to herein, steady state conditions represent a range of conditions under which the process can operate acceptably for extended periods of time. Within the range of conditions, a target set of conditions are typically specified. During normal steady state operation, the sampling, control and cull system referred to above continually monitors both product and process conditions, and makes adjustments as appropriate to maintain or urge the process and product conditions toward respective target sets of such conditions. Namely, when deviations from one or both of the product or process target set of conditions become sufficiently great to trigger a response, the control system makes adjustments to one or more operating conditions in order to drive the process toward the respective target set or sets of conditions.

While the above teaching illustrates the invention with respect to controlling a manufacturing process, the invention applies as well to any process whether, for example and without limitation, a manufacturing type process, a service business process, a method of doing business, a process for handling electronic data or other information, or a computer operating system, whether hardware or software, or both.

The population of product produced using an above described process has an improved balance between actual cull/ship decisions and the actual acceptability of the product shipped, based on the acceptable output parameters. Namely, the shipped product population has relatively fewer defective units of product and/or the culled product has relatively fewer acceptable units of product.

In view of the above described conditions for product sampling and culling, the invention contemplates a statistical control model based on the assumptions of two general sets of process conditions, and a two or more part product population. The first part of the product population is produced during the first set of process conditions, namely steady state conditions. The second part of the product population is produced during the second set of process conditions, namely the destabilizing event window. The statistical control model uses a first set of assumptions based on steady state conditions for monitoring and controlling units produced during steady state conditions, and a second set of assumptions based on rapidly fluctuating conditions in the destabilizing event window for monitoring and controlling units produced during destabilizing event windows. Further, the statistical control model of the invention can apply a third set of assumptions for monitoring and controlling product produced during destabilizing event windows wherein the destabilizing event has little or no direct affect on operating speed of the process.

Figure 8:
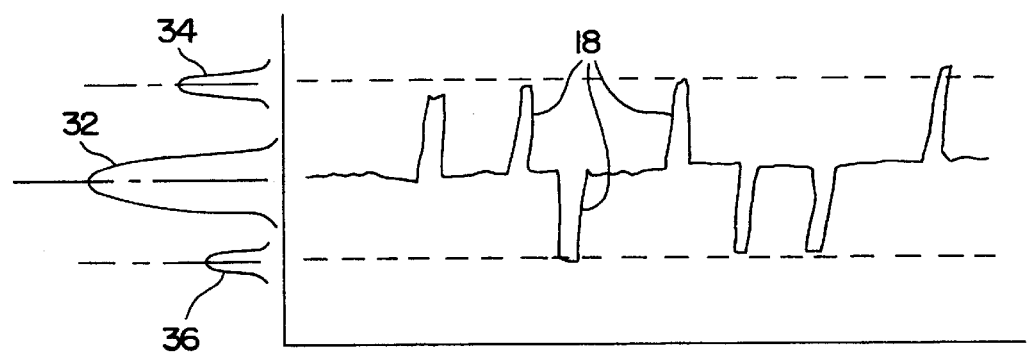
FIG. 8 illustrates a control model of the invention based on a three-segment population.

FIGS. 7 and 8 illustrate the difference between population assumptions for the single segment and multiple segment populations. As illustrated in FIG. 7, the assumption of a single population can result in a relatively broader population distribution wherein the control model accepts frequent destabilizing events 18 as being within normal operation of the process, and thereby is unable to recognize the anomalous behavior of destabilizing events 18 as anomalous.

Referring now to FIG. 8, the control model of the invention recognizes a multiple segment population, namely a core population segment 32, an upper population segment 34, and a lower population segment 36. The core population segment represents steady state operation. The upper and lower population segments represent anomalous destabilizing events, and according to the invention, can be recognized and identified as such. According to the invention, the operating conditions relating to each unit of product identifies that unit of product with respect to one of the multiple segments of the population. Once the population segment has been identified, the control system can automatically respond in terms of the respective population segment. Specifically, the control system can more accurately define steady state conditions by eliminating from the steady state population segment the anomalous behavior which occurs during destabilizing event conditions, thereby identifying a more narrowly-defined steady state population segment. By identifying a more narrowly-defined steady state population segment, the control system has a more narrowly-defined set of operating conditions according to which to control operation of the process, whereby true anomalies, such as destabilizing events, can be better identified, and better controlled.

The invention has so far been described in terms of manufacturing processes, and the invention can be applied to a wide variety of manufacturing process. The control methods, statistical control models, and output populations of the invention, without limitation, can be as well applied widely to production of services, to methods of doing business, processes for handling electronic data or other information, and computer operating systems whether hardware or software, or both. While the inventors recognize that the operating environments, and underlying fact sets will be substantially different for such service operations, methods of doing business, processes for handling electronic data or other information, and computer operating systems, the principles by which such systems are controlled are sufficiently described herein that such principles can now be applied in such settings to achieve results corresponding to the benefits described herein.

Those skilled in the art will now see that certain modifications can be made to the apparatus and methods herein disclosed with respect to the illustrated embodiments, without departing from the spirit of the instant invention. And while the invention has been described above with respect to the preferred embodiments, it will be understood that the invention is adapted to numerous rearrangements, modifications, and alterations, and all such arrangements, modifications, and alterations are intended to be within the scope of the appended claims.

To the extent the following claims use means plus function language, it is not meant to include there, or in the instant specification, anything not structurally equivalent to what is shown in the embodiments disclosed in the specification.

Having thus described the invention, what is claimed is:

1. A method of controlling a process having operating conditions, one or more inputs, and one or more outputs, the process defining parameters of the one or more outputs, the method comprising:
   (a) defining a first steady state set of first respective ones of the operating conditions representing one or more previously-specified acceptable operating parameters of the process;
   (b) defining a second steady state set of output conditions representing acceptable parameters of the one or more outputs;
   (c) operating the process, and routinely sampling output on the basis of a single output population model;
   (d) detecting destabilizing process events which result in output not representing acceptable output parameters;
   (e) defining one or more third sets of operating conditions according to which output is rejected and/or defining one or more fourth sets of output parameters according to which output is rejected;
   (f) upon detecting a destabilizing process event in step (d), temporarily implementing sampling assuming a dual population output, including
      1) automatically rejecting output whenever any one of the operating conditions or output parameters of step (e) is violated, thereby establishing a leading automatic output rejection and a trailing automatic output rejection, and thus defining an automatic output rejection period according to which output is automatically rejected in response to the destabilizing event, and
      2) defining a leading transition period proximate and before the automatic output rejection period, and a trailing transition period proximate and after the automatic output rejection period, the transition periods, overall, representing periods of higher than average risk that output will be defective; and
   (g) identifying output in at least one of the leading transition period and the trailing transition period.

2. A method as in claim 1, including automatically sampling output in at least one of the leading transition period and the trailing transition period, and including returning to routinely sampling output based on a single output population model when both the operating parameters and output conditions indicate the existence of acceptable previously-specified steady state conditions, and no new destabilizing event has been detected.

3. A method as in claim 1, including automatically sampling output from both the leading transition period and the trailing transition period.

4. A method as in claim 1, including evaluating transition period output against previously-specified acceptable output parameters and making a reject/accept decision based on the evaluation.

5. A method as in claim 4 including, when transition period output is rejected, further sampling and manually evaluating output which is farther away, chronologically in time, or by number of units of product, respectively before or after, the automatic rejection period.

6. A method as in claim 1, including manually evaluating transition period output against previously-specified acceptable output parameters and making adjustments to the process based on the evaluation.

7. A method as in claim 1, including operating the process at steady state conditions within the specified acceptable parameters at least one of before a leading transition period or after a trailing transition period, and defining a respective beginning or end of the respective transition period away from the automatic output rejection period.

8. A method as in claim 1, including compiling and evaluating data representing numerous ones of the transition periods and thereby developing desirable adjustments to a length of at least one of the transition periods and correspondingly adjusting the respective transition period in which samples are automatically collected.

9. A method as in claim 8 wherein the adjustment of the respective transition period results in an improved balance between actual accept/reject decisions and the actual acceptability of the output based on the acceptable output parameters.

10. A method as in claim 1, the routine sampling being based on steady state operating conditions.

11. A method as in claim 1, the detected destabilizing events comprising events which have little or no direct affect on operating speed of the process.

12. A method as in claim 1, the detected destabilizing events comprising events which have substantial direct affect on operating speed of the process, including shutting the process down.

13. A method as in claim 1, including sampling transition period output, evaluating the transition period samples, and managing operation of the process based on the results of the evaluation.

14. A method of controlling a process having operating conditions, one or more inputs, and one or more outputs, the process defining parameters of the one or more outputs, the method comprising:
   (a) defining a first steady state set of first respective ones of the operating conditions representing one or more previously-specified acceptable operating parameters of the process;

(b) defining a second steady state set of output conditions representing acceptable parameters of the one or more outputs;

(c) operating and controlling the process, and routinely sampling output on the basis of (i) a first output population segment produced under substantially steady state conditions and (ii) at least a second output population segment produced pursuant to destabilizing process events;

(d) routinely sampling output on the basis of steady state operation during steady state operation;

(e) detecting destabilizing process events which result in output not representing acceptable output parameters;

(f) defining one or more third sets of operating conditions according to which output is rejected and/or defining one or more fourth sets of output parameters according to which output is rejected;

(g) upon detecting a destabilizing process event in step (e), temporarily implementing output identification, and operations management, on the basis of the population segment typically produced pursuant to the respective type of extant destabilizing process event; and (h) when both operating parameters and output conditions indicate existence of acceptable steady state condition, and no new destabilizing event has been detected, returning to sampling output on the basis of steady state operation.

15. A method as in claim 1, including automatically rejecting output whenever any one of the operating conditions or output parameters of step (f) is violated, thereby establishing a leading automatic output rejection and a trailing automatic output rejection, and thus defining an automatic output rejection period according to which output is automatically rejected in response to the destabilizing event, and defining a leading transition period proximate and before the automatic output rejection period, and a trailing transition period proximate and after the automatic output rejection period, the transition periods, overall, representing periods of higher than average risk that output will be defective.

16. A method as in claim 15, including automatically sampling output from both the leading transition period and the trailing transition period.

17. A method as in claim 15, including evaluating transition period output against previously-specified acceptable output parameters and making a reject/accept decision based on the evaluation.

18. A method as in claim 17 including, when transition period output is rejected, further sampling and manually evaluating output which is farther away, chronologically in time, or by number of units of product, respectively before or after, the automatic rejection period.

19. A method as in claim 15, including manually evaluating transition period output against previously-specified acceptable output parameters and making adjustments to the process based on the evaluation.

20. A method as in claim 15, including operating the process at steady state conditions within the specified acceptable parameters at least one of before a leading transition period or after a trailing transition period, and defining a respective beginning or end of the respective transition period away from the automatic output rejection period.

21. A method as in claim 15, including compiling and evaluating data representing numerous ones of the transition periods and thereby developing desirable adjustments to a length of at least one of the transition periods and correspondingly adjusting the respective transition period in which samples are automatically collected.

22. A method as in claim 21 wherein the adjustment of the respective transition period results in an improved balance between actual accept/reject decisions and the actual acceptability of the output based on the acceptable output parameters.

23. A method as in claim 14, the detected destabilizing events comprising events which have little or no direct affect on operating speed of the process.

24. A method as in claim 14, the detected destabilizing events comprising events which have substantial direct affect on operating speed of the process, including shutting the process down.

25. A method as in claim 15, including sampling transition period output, evaluating the transition period samples, and managing operation of the process based on the results of the evaluation.

26. A statistical control model for controlling a process having operating conditions, one or more inputs, and one or more outputs, the process defining parameters of the one or more outputs, the statistical control model comprising:

(a) defining a first steady state set of first respective ones of the operating conditions representing one or more acceptable operating parameters of the process, and target operating parameters included therein;

(b) defining a second steady state set of output conditions representing acceptable parameters of the one or more outputs, and target output parameters included therein;

(c) operating the process, and routinely sampling output on the basis of a single output population model;

(d) detecting destabilizing process events which result in output not representing acceptable output parameters;

(e) defining one or more third sets of operating conditions according to which output is rejected and/or defining one or more fourth sets of output parameters according to which output is rejected;

(f) upon detecting a destabilizing process event in step (d), temporarily implementing sampling assuming a dual population output, including 1) automatically rejecting output whenever any one of the operating conditions or output parameters of step (e) is violated, thereby establishing a leading automatic output rejection and a trailing automatic output rejection, and thus defining an automatic output rejection period according to which output is automatically rejected in response to the destabilizing event, and 2) defining a leading transition period proximate and before the automatic output rejection period, and a trailing transition period proximate and after the automatic output rejection period, the transition periods, overall, representing periods of higher than average risk that output will be defective; and (g) identifying output in at least one of the leading transition period and the trailing transition period.

27. A statistical control model as in claim 26, including automatically sampling output in at least one of the leading transition period and the trailing transition period, and including returning to routinely sampling output based on a single output population model when both the operating parameters and output conditions indicate the existence of acceptable steady state conditions, and no new destabilizing event has been detected.

28. A statistical control model as in claim 26, including automatically sampling output from both the leading transition period and the trailing transition period.

29. A statistical control model as in claim 26, including evaluating transition period output against the acceptable output parameters and making a reject/accept decision based on the evaluation.

30. A statistical control model as in claim 29 including, when transition period output is rejected, further sampling and manually evaluating output which is farther away, chronologically in time or by number of units of product, respectively before or after, the automatic rejection period.

31. A statistical control model as in claim 26, including manually evaluating transition period output against the acceptable output parameters and making adjustments to the process based on the evaluation.

32. A statistical control model as in claim 26, including operating the process at steady state conditions within the acceptable parameters at least one of before a leading transition period or after a trailing transition period, and defining a respective beginning or end of the respective transition period away from the automatic output rejection period.

33. A statistical control model as in claim 26, including compiling and evaluating data representing numerous ones of the transition periods and thereby developing desirable adjustments to a length of at least one of the transition periods and correspondingly adjusting the respective transition period in which samples are automatically collected.

34. A statistical control model as in claim 33 wherein the adjustment of the respective transition period results in an improved balance between actual accept/reject decisions and the actual acceptability of the output based on the acceptable output parameters.

35. A statistical control model as in claim 26, the routine sampling being based on steady state operating conditions.

36. A statistical control model as in claim 26, the detected destabilizing events comprising events which have little or no direct affect on operating speed of the process.

37. A statistical control model as in claim 26, the detected destabilizing events comprising events which have substantial direct affect on operating speed of the process, including shutting the process down.

38. A statistical control model as in claim 26, including sampling transition period output, evaluating the transition period samples, and managing operation of the process based on the results of the evaluation.

39. A multiple-segment product population, comprising:
  (a) a not-culled population segment comprising predominantly acceptable members of the population; and
  (b) a culled population segment comprising a steady state cull element, an automatic cull segment, and a transition inspection cull segment, the culled population segment representing
    (i) defining a first steady state set of operating conditions representing one or more acceptable operating parameters, and target operating parameters included therein;
    (ii) defining a second steady state set of output conditions representing acceptable output parameters, and target output parameters included therein;
    (iii) routinely sampling output on the basis of a single output population model;
    (iv) detecting destabilizing events which result in output not representing acceptable output;
    (v) defining one or more third sets of operating conditions according to which output is culled and/or defining one or more fourth sets of output parameters according to which output is culled;
    (vi) upon detecting a destabilizing event in step (iv), temporarily implementing sampling according to a dual population output, including
      1) automatically rejecting output whenever any one of the operating conditions or output parameters of step (v) are violated, thereby establishing a leading automatic output cull and a trailing automatic output cull, and thus defining an automatic output cull period according to which output is automatically culled in response to the destabilizing event, and
      2) defining a leading transition period proximate and prior to the automatic output rejection period, and a trailing transition period proximate and after the automatic output rejection period, the transition periods, overall, representing periods of higher than average risk that output will be defective; and
    (vii) identifying output in at least one of the leading transition period and the trailing transition period.

40. A product population as in claim 39, the transition inspection cull segment representing automatically sampling output in at least one of the leading transition period and the trailing transition period, and returning to routinely sampling output based on a single output population model when both the operating parameters and output conditions indicate the existence of acceptable steady state conditions, and no new destabilizing event has been detected.

41. A product population as in claim 39, the transition inspection cull segment representing automatically sampling output from both the leading transition period and the trailing transition period.

42. A product population as in claim 39, the transition inspection cull segment representing evaluating transition period output against the acceptable output parameters and making a reject/accept decision based on the evaluation.

43. A product population as in claim 42, the transition inspection cull segment representing, when transition period output is rejected, further sampling and manually evaluating output which is farther away, chronologically in time or in number of units of product, respectively before or after, the automatic rejection period.

44. A product population as in claim 39, the transition inspection cull segment representing manually evaluating transition period output against the acceptable output parameters and making adjustments to the process based on the evaluation.

45. A product population as in claim 39, the transition inspection cull segment representing operating the process at steady state conditions within the acceptable parameters at least one of before a leading transition period or after a trailing transition period, and defining a respective beginning or end of the respective transition period away from the automatic output rejection period.

46. A product population as in claim 39, the transition inspection cull segment representing compiling and evaluating data representing numerous ones of the transition periods and thereby developing desirable adjustments to a length of at least one of the transition periods and correspondingly adjusting the respective transition period in which samples are automatically collected.

47. A product population as in claim 39, the routine sampling being based on steady state operating conditions.

48. A product population as in claim 39, the detected destabilizing events comprising events which have little or no direct affect on operating speed of the process.

49. A product population as in claim 39, the detected destabilizing events comprising events which have substantial direct affect on operating speed of the process, including shutting the process down.

* * * * *

UNITED STATES PATENT AND TRADEMARK OFFICE
CERTIFICATE OF CORRECTION

PATENT NO. : 6,260,188 B1
DATED : July 10, 2001
INVENTOR(S) : Tanakon Ungpiyakul et al.

It is certified that error appears in the above-identified patent and that said Letters Patent is hereby corrected as shown below:

<u>Title page,</u>
Item [56], delete "9081233", and substitute -- 9081233A --.

<u>Column 13,</u>
Line 33, delete "triggerlevel", and substitute -- trigger level --.

<u>Column 17,</u>
Line 20, delete "68", and substitute -- 6B --.

<u>Column 19,</u>
Line 6, delete "process", and substitute -- processes --.

Signed and Sealed this

Twenty-fifth Day of December, 2001

Attest:

*Attesting Officer*

JAMES E. ROGAN
*Director of the United States Patent and Trademark Office*